United States Patent
Shin et al.

(10) Patent No.: US 12,292,407 B2
(45) Date of Patent: May 6, 2025

(54) MEASURING ION STRENGTH USING CLOSED-LOOP ELECTROCHEMICAL PH MODULATION

(71) Applicant: Robert Bosch GmbH, Stuttgart (DE)

(72) Inventors: Young Shik Shin, Mountain View, CA (US); Nadezda Fomina, Redwood City, CA (US); Christopher Johnson, San Carlos, CA (US); Armin Darvish, Brisbane, CA (US); Christoph Lang, Sunnyvale, CA (US)

(73) Assignee: Robert Bosch GmbH, Stuttgart (DE)

( * ) Notice: Subject to any disclaimer, the term of this patent is extended or adjusted under 35 U.S.C. 154(b) by 375 days.

(21) Appl. No.: 17/184,274

(22) Filed: Feb. 24, 2021

(65) Prior Publication Data

US 2022/0268729 A1 Aug. 25, 2022

(51) Int. Cl.
*G01N 27/416* (2006.01)
*C12Q 1/6851* (2018.01)
*G05D 21/02* (2006.01)

(52) U.S. Cl.
CPC ....... *G01N 27/4167* (2013.01); *C12Q 1/6851* (2013.01); *G05D 21/02* (2013.01)

(58) Field of Classification Search
CPC ............ G01N 27/4167; G01N 27/302; G01N 27/414; G01N 27/4145; C12Q 1/6851; G05D 21/02
See application file for complete search history.

(56) References Cited

U.S. PATENT DOCUMENTS

| | | |
|---|---|---|
| 9,075,041 B2 | 7/2015 | Kavusi et al. |
| 9,469,870 B2 | 10/2016 | Amura et al. |
| 9,766,197 B2 | 9/2017 | Johnson et al. |
| 9,840,733 B2 | 12/2017 | Lamura et al. |
| 9,874,538 B2 | 1/2018 | Johnson et al. |
| 9,910,008 B2 | 3/2018 | Johnson et al. |
| 10,011,549 B2 | 7/2018 | Johnson et al. |
| 10,041,905 B2 | 8/2018 | Johnson et al. |
| 10,379,080 B2 | 8/2019 | Johnson et al. |

(Continued)

FOREIGN PATENT DOCUMENTS

| | | | |
|---|---|---|---|
| EP | 2251435 A1 * | 11/2010 | ........... C12Q 1/6851 |
| EP | 2823294 B1 | 5/2016 | |
| WO | 2017005587 A1 | 1/2017 | |

OTHER PUBLICATIONS

Fomina et al., "An electrochemical platform for localized pH control on demand", Lab Chip, vol. 16, 2016, pp. 2236-2244.

(Continued)

*Primary Examiner* — Luan V Van
*Assistant Examiner* — Shizhi Qian
(74) *Attorney, Agent, or Firm* — Michael Best & Friedrich LLP (57) ABSTRACT

Provided is a method for monitoring a change of ion strength in a sample solution by a closed-loop device that provides continuous cycling of electrochemical pH modulation between pre-defined pH values. In particular, the change of ion strength may be induced by a chemical reaction and may ultimately alter the electrical control parameters of the closed-loop device. By measuring such electrical control parameters, the degree and progress of the underlying chemical reaction may be monitored.

12 Claims, 6 Drawing Sheets

(56) References Cited

U.S. PATENT DOCUMENTS

| | | | |
|---|---|---|---|
| 2010/0151479 A1* | 6/2010 | Toumazou | C12Q 1/6825 |
| | | | 435/287.2 |
| 2013/0220830 A1* | 8/2013 | Paulus | G01N 30/06 |
| | | | 204/263 |
| 2016/0003766 A1* | 1/2016 | Johnson | G01N 33/5306 |
| | | | 205/792 |
| 2016/0202202 A1* | 7/2016 | Wu | G01N 27/302 |
| | | | 156/278 |
| 2017/0010238 A1 | 1/2017 | Johnson et al. | |
| 2017/0016058 A1* | 1/2017 | Lamura | C12Q 1/6844 |
| 2019/0017954 A1* | 1/2019 | Shin | G01N 33/5438 |
| 2019/0137444 A1 | 5/2019 | Johnson et al. | |
| 2020/0238196 A1* | 7/2020 | Nagy | B01F 35/7176 |

OTHER PUBLICATIONS

Martin et al., "Ultimate single-copy DNA detection using real-time electrochemical LAMP", ACS Sens., vol. 1, No. 7, 2016, pp. 904-912.

Salm et al., "Electrical Detection of Nucleic Acid Amplification Using an On-Chip Quasi-Reference Electrode and a PVC REFET", Anal. Chem., vol. 86, 2014, pp. 6968-6975.

Toumazou et al., "Simultaneous DNA amplification and detection using a pH-sensing semiconductor system", Nature Methods, 2013, vol. 10, No. 7, pp. 641-646.

U.S. Appl. No. 16/931,727, filed Jul. 17, 2020 by Shin et al.

\* cited by examiner

MEASURING ION STRENGTH USING CLOSED-LOOP ELECTROCHEMICAL PH MODULATION

FIELD

The present disclosure relates to methods of monitoring the progress of a chemical reaction in a solution by a closed-loop device capable of electrochemical pH modulation.

BACKGROUND pH plays an important role in the inter-molecular interactions, chemical modification, enzymatic activities, chemical/biochemical reaction kinetics, and visualization of pH sensitive reporter molecules. Since pH can serve as a universal switch or a controller for various types of processes, monitoring pH over time helps to make sure the experimental condition is still within the valid and expected range over the whole process of an experiment. On the other hand, pH can be a good indicator of the degree and progress of reactions of interest because biological or chemical reactions often introduce the ion concentration change within the sample solution. In the beginning of this process, such change is still compensated by the buffering capacity of the buffer solution and pH is maintained for a while until the ion concentration change exceeds the buffering capacity.

Typically quantitative Polymerase Chain Reaction (qPCR) uses optical characterization to determine the progression of the PCR reaction where the fluorescence signal of an intercalating dye is proportional to the amount of DNA in the sample. As PCR progresses the quantity of DNA is monitored by fluorescence and by analysis of the exponential change in signal during cycling the original concentration of DNA can be quantitatively determined. It is also possible to monitor and quantify the PCR progress using pH sensing as the incorporation of nucleotides during PCR releases protons as a byproduct. The change in pH can therefore be correlated to the amount of DNA, and monitoring the pH change during the exponential phase of DNA replication can be used to quantify the original DNA concertation Direct measurement of pH change was reported, for example, as a method for detecting and quantifying the progress of DNA amplification in a qPCR process. This approach works favorably in a weakened buffer that allows for pH change caused by the studied reaction (DNA amplification). In this scenario, diluted buffer solution is used in order to increase the measurement sensitivity. Any change to pH, however, can complicate the direct correlation to the original DNA as the enzyme efficiency is also regulated to an extent by the pH of the solution. As diluted buffer solution is used, there is a risk that enzyme efficiency may be compromised. Therefore, monitoring the pH of solution would require deconvolution of this contribution to the DNA quantification calculation. The same problem remains for optical systems where a change in pH of the sample would not be captured by the optical readout.

Thus, there remains a need for a method for monitoring a chemical reaction with high sensitivity in a constant pH environment, which measures ion concentration change in an early stage of the chemical reaction, maintains the functionality of any pH-sensitive components of the reaction (e.g., enzymes), avoids the need for deconvolution as the reaction progresses, and more desirably offers faster detection and improved stability to biosensors and bioreactors.

SUMMARY

In one aspect, the present disclosure provides a method for monitoring a chemical reaction, comprising
  (a) starting the chemical reaction in a buffered solution equipped with a closed-loop device, wherein
    the buffered solution comprises a pH modulating agent;
    the closed-loop device comprises an electronic controller, a working electrode, a counter electrode, a reference electrode, and a sensing element, wherein the working electrode, the counter electrode, the reference electrode, and the sensing element are immersed in the buffered solution; and
    the chemical reaction causes a change of ionic strength of the buffered solution;
  (b) applying a current or voltage to the working electrode, whereupon the pH modulating agent causes a change of a pH value in a zone adjacent to the surface of the working electrode;
  (c) detecting the change of ionic strength of the buffered solution with the closed-loop device.

Other aspects, features, and embodiments will become apparent by consideration of the detailed description and accompanying drawings.

DETAILED DESCRIPTION

Before any embodiments are explained in detail, it is to be understood that this disclosure is not intended to be limited in its application to the details of construction and the arrangement of components set forth in the following description or illustrated in the following drawings. Embodiments are capable of other configurations and of being practiced or of being carried out in various ways.

The present disclosure provides a method for monitoring a chemical reaction in a solution by a closed-loop device through measurement of a change of ion strength in the solution. Advantageously, the present method may be used to monitor chemical and biological reactions at an early stage with high sensitivity while the pH of the solution remains constant.

The terms "comprise(s)," "comprising," "include(s)," "including," "having," "has," "contain(s)," "containing," and variants thereof, as used herein, are open-ended transitional phrases, terms, or words that are meant to encompass the items listed thereafter and equivalents thereof as well as additional items. The singular forms "a", "and", and "the" include plural references unless the context clearly dictates otherwise. Where the term "comprising" is used, the present disclosure also contemplates other embodiments "comprising", "consisting of", and "consisting essentially of", the embodiments or elements presented herein, whether explicitly set forth or not.

Any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

In one aspect, the present disclosure provides a method for monitoring a chemical reaction, comprising
(a) starting the chemical reaction in a buffered solution equipped with a closed-loop device, wherein
the buffered solution comprises a pH modulating agent;
the closed-loop device comprises an electronic controller, a working electrode, a counter electrode, a reference electrode, and a sensing element, wherein the working electrode, the counter electrode, the reference electrode, and the sensing element are immersed in the buffered solution; and
the chemical reaction causes a change of ionic strength of the buffered solution;
(b) applying a current or voltage to the working electrode, whereupon the pH modulating agent causes a change of a pH value in a zone adjacent to the surface of the working electrode;
(c) detecting the change of ionic strength of the buffered solution with the closed-loop device.

The chemical reaction as described herein includes any chemical and biological processes in a solution that produces positively charges ions and/or negatively charged ions, such as $H^+$, $Na^+$, $K^+$, $OH^-$ and $Cl^-$, which causes a change in the ion concentration or ion strength of the solution. In some embodiments, the chemical reaction produces hydrogen ion ($H^+$) or hydroxide ion ($OH^-$). In particular embodiments, the chemical reaction produces $H^+$.

The buffered solution refers to an aqueous or organic solution that may maintain its pH value at a nearly constant level and does not interfere with the chemical reaction being studied or the operation of the closed-loop device. In some embodiments, the buffered solution is an aqueous solution comprising a buffering agent. Suitable buffering agents include, but are not limited to, phosphate, acetate, {[tris (hydroxymethyl)methyl]amino}propanesulfonic acid (TAPS), N,N-bis(2-hydroxyethyl)glycine (Bicine), tris(hydroxymethyl)aminomethane (Tris), N-tris(hydroxymethyl) methylglycine (Tricine), 3-[N-Tris(hydroxymethyl)methyl-amino]-2-hydroxypropanesulfonic acid (TAPSO), 4-(2-hydroxyethyl)-1-piperazineethanesulfonic acid (HEPES), {[tris(hydroxymethyl)methyl]amino}ethanesulfonic acid (TES), 3-(N-morpholino)propanesulfonic acid (MOPS), piperazine-N,N'-bis(2-ethanesulfonic acid) (PIPES), dimethylarsinic acid (cacodylate), saline sodium citrate (SSC), 2-(N-morpholino)ethanesulfonic acid (MES), and other buffers used in known biological applications. In some embodiments, the buffered solution is a solution in which a biological event, such as protein binding, DNA replication, enzymatic hydrolysis, or enzymatic synthesis may be detected or monitored.

The buffering capacity of the buffered solution relates to the concentration of the buffering agent. The buffering agent may be present at a concentration of at least 1 mM, at least 5 mM, at least 10 mM, at least 50 mM, at least 100 mM, or at least 500 mM. In some embodiments, the concentration of the buffering agent is at least 5 mM. In some embodiments, the concentration of the buffering agent is about 5 mM to about 500 mM, such as about 5 mM to about 250 mM, about 10 mM to about 250 mM, or about 50 mM to about 250 mM.

In some embodiments, chemical reactions involved in known biological processes such as cellular signal transduction, metabolism, and cell growth and reproduction may be studied. The chemical reaction may include a biospecimen or a sample derived from the biospecimen. The biospecimen may be a fluid from an animal, a fixed tissue, cells such as fixed cells and live cells, extracellular vesicles, and surface patterned biomolecules such as proteins, DNAs, RNAs, and peptides, or combinations thereof. In some embodiments, the chemical reaction includes a biomolecule, such as a DNA, an RNA, or a peptide derived from an animal or a cell.

In some embodiments, the chemical reaction is a DNA amplification reaction. In some embodiments, the chemical reaction is a quantitative Polymerase Chain Reaction (qPCR). Sample preparation and the qPCR experiment may be carried out using known techniques. For example, during the PCR reaction in a solution, hydrogen ion ($H^{3O}$) are released as the nucleotides are incorporated in the growing nucleic acid chain, thus changing the ion strength of the solution, which may be detected and quantitated by the present method.

The buffered solution absorbs excess $H^+$ or $OH^-$ to maintain pH. The present method may actively increase $H^+$ or $OH^-$ near the surface of the electrodes, thereby changing the pH near the electrodes. As reaction progresses, the buffering capability of the solution may become weaker as the buffering agents are consumed, which may eventually change the pH of the solution. In some embodiments, the present method may detect the change of ion strength in the solution before the pH change is measurable.

Advantageously, the present method may be used to detect and quantitate the degree of the underlying chemical reaction (e.g., qPCR) by measuring the change of ionic strength of the buffered solution, while the pH of the solution is maintained virtually constant. In particular embodiments, the present method measures the change of ionic strength of the buffered solution, while the buffered solution maintains a constant pH value. Thus, the present method may be used to monitor a chemical or biological process without disturbing the function of any pH sensitive components (e.g., enzymes) involved in such process.

The pH modulating agent refers to a compound or a composition that undergoes a chemical reaction in a solution in response to electrical potentials or currents thereby causing a change in the pH value of the solution. The chemical reaction may be a redox reaction, in which the redox state of the pH modulating agent is changed. Electrochemical oxidation and/or reduction of the pH modulating agents via electrical stimulus may introduce local pH change through the equilibration between generation or consumption of protons and buffering capacity of the buffer solution. This may generate a pH modulation zone with a very short vertical distance, for example from several nm to several μm, from the surface of the electrode. In some embodiments, the pH modulating agents may include materials that can perform proton coupled electron transfer. Suitable pH modulating agents include, but are not limited to quinone derivatives, aminophenol derivatives, aniline derivatives, benzidine derivatives, hydrazine derivatives, phenol-Ru(2,2'-bipyridine)$_3^{2+}$, and combinations thereof. Suitable pH modulating agents may also include other known compounds having pH-responding moieties not exemplified above.

In some embodiments, the pH modulating agent is a quinone derivative of any of formula (I)-(XII)

(I)

(II)

(III)

(IV)

(V)

(VI)

(VII)

-continued wherein $R_1$, $R_2$, $R_3$, $R_4$, $R_6$, $R_6$, $R_7$, and $R_8$ are each independently selected from the group consisting of: H; $C_nH_{2n+1}$; Cl; F; I; Br, OM, $NO_2$, OH, $OC_nH_{2n+1}$, $OC_nH_{2n}OH$, $O(C_nH_{2n}O)_yH$, $O(C_nH_{2n}O)_yC_nH_{2n+1}$, $O(C_nH_{2n}O)_yCOOH$; $O(C_nH_{2n}O)_yCOOM$; COOH; COOM; $COOC_nH_{2n+1}$;
$CONHC_nH_{2n+1}$; $CON(C_nH_{2n+1})_2$; $SO_3H$; $SO_3M$; $NH_2$; $NHC_nH_{2n+1}$; $N(C_nH_{2n+1})_2$; $NHC_nH_{2n}OH$;
$NHC_nH_{2n}NH_2$; $N(C_nH_{2n}OH)_2$; $N(C_nH_{2n}NH_2)_2$; $NHCOC_nH_{2n+1}$; $NC_nH_{2n}COC_nH_{2n+1}$;
$NC_nH_{2n}COC_nH_{2n}OH$; $NC_nH_{2n}COC_nH_{2n}NH_2$; $NHC_nH_{2n}COC_nH_{2n}SH$; SH; $SC_nH_{2n+1}$; $SC_nH_{2n}OH$;
$S(C_nH_{2n}O)_yH$; $S(C_nH_{2n}O)_yC_nH_{2n+1}$; $S(C_nH_{2n}O)_yCOOH$; $S(C_nH_{2n}O)_yCOOM$; $OC_nH_{2n}SH$;
$O(C_nH_{2n}O)_yC_nH_{2n}SH$; $O(C_nH_{2n}O)_yC_nH_{2n}SC_nH_{2n+1}$; $C_nH_{2n}OC_nH_{2n+1}$; $C_nH_{2n}SC_nH_{2n+1}$;
$C_nH_{2n}NHC_nH_{2n+1}$; $C_nH_{2n}OH$; $C_nH_{2n}OC_nH_{2n+1}$; $C_nH_{2n}OC_nH_{2n}OH$; $C_nH_{2n}O(C_nH_{2n}O)_yCOOH$;
$C_nH_{2n}O(C_nH_{2n}O)_yCOOM$; $C_nH_{2n}COOH$; $C_nH_{2n}COOM$; $C_nH_{2n}COOC_nH_{2n+1}$;
$C_nH_{2n}CONHC_nH_{2n+1}$; $C_nH_{2n}CONH(C_nH_{2n+1})_2$; $C_nH_{2n}SO_3H$; $C_nH_{2n}SO_3M$; $C_nH_{2n}NH_2$;
$C_nH_{2n}N(C_nH_{2n+1})_2$; $C_nH_{2n}NHC_nH_{2n}OH$; $C_nH_{2n}NHC_nH_{2n}NH_2$; $C_nH_{2n}N(C_nH_{2n}OH)_2$;
$C_nH_{2n}N(C_nH_{2n}NH_2)_2$; $C_nH_{2n}NHCOC_nH_{2n+1}$; $C_nH_{2n}NHC_nH_{2n}COC_nH_{2n}OH$;
$C_nH_{2n}NHC_nH_{2n}COC_nH_{2n}NH_2$; $C_nH_{2n}NHC_nH_{2n}COC_nH_{2n}SH$; $C_nH_{2n}SH$; $C_nH_{2n}SC_nH_{2n+1}$;
$C_nH_{2n}SC_nH_{2n}OH$; $C_nH_{2n}S(C_nH_{2n}O)_yH$; $C_nH_{2n}S(C_nH_{2n}O)_yC_nH_{2n+1}$; $C_nH_{2n}S(C_nH_{2n}O)_y$ $C_nH_{2n}COOH$;
$C_nH_{2n}S(C_nH_{2n}O)_yC_nH_{2n}COOM$; sugars; peptides; and amino acids,
wherein
M is any metal cation or $NH_4^+$,
n is an integer from 1 to $10^9$, and
y is an integer from 1 to $10^9$.

In some embodiments, $R_1$, $R_2$, $R_3$, $R_4$, $R_5$, $R_6$, $R_7$, and $R_8$ are each independently selected from the group consisting $C_nH_{2n}OH$; $C_nH_{2n}OC_nH_{2n}OH$; $C_nH_{2n}O(C_nH_{2n}O)_yCOOH$;
$C_nH_{2n}O(C_nH_{2n}O)_yCOOM$; $C_nH_{2n}COOH$; $C_nH_{2n}COOM$; $C_nH_{2n}COOC_nH_{2n+1}$;
$C_nH_{2n}CONHC_nH_{2n+1}$; $C_nH_{2n}CONH(C_nH_{2n+1})_2$; $C_nH_{2n}SO_3H$; $C_nH_{2n}SO_3M$; $C_nH_{2n}NH_2$;
$C_nH_{2n}NHC_nH_{2n+1}$; $C_nH_{2n}N(C_nH_{2n+1})_2$; $C_nH_{2n}NHC_nH_{2n}OH$; $C_nH_{2n}NHC_nH_{2n}NH_2$;
$C_nH_{2n}N(C_nH_{2n}OH)_2$; $C_nH_{2n}N(C_nH_{2n}NH_2)_2$; $C_nH_{2n}NHCOC_nH_{2n+1}$; $C_nH_{2n}NC_nH_{2n}COC_nH_{2n}OH$;
$C_nH_{2n}NC_nH_{2n}COC_nH_{2n}NH_2$; $C_nH_{2n}NC_nH_{2n}COC_nH_{2n}SH$; $C_nH_{2n}SH$; $C_nH_{2n}SC_nH_{2n}OH$;
$C_nH_{2n}S(C_nH_{2n}O)_yOH$; $C_nH_{2n}S(C_nH_{2n}O)_yH$; $C_nH_{2n}S(C_nH_{2n}O)_yC_nH_{2n+1}$;
$C_nH_{2n}S(C_nH_{2n}O)_yC_nH_{2n}COOH$; and $C_nH_{2n}S(C_nH_{2n}O)_yC_nH_{2n}COOM$. In some embodiments, the pH modulating agent is a quinone derivative of formula (I).

Suitable quinone derivatives may contain various functional groups to tune their solubility, biocompatibility, and electrochemical properties. Other examples of suitable quinone derivatives include those described in U.S. Pat. Nos. 9,766,197, 9,874,538, 9,910,008, 10,011,549, 10,041,905, US 2017/0010238, and WO 2017/005587, the entire contents of which are incorporated herein by reference.

The closed-loop control device may include a set of electrodes, for example, a working electrode, a sensing element, a counter electrode, and a reference electrode. The reference electrode provides a stable potential reference for measurement. In some implementations, when the sensing element has good stability and is placed in a stable pH solution, the sensing element is used as a reference electrode. Further, in some implementations, the counter and reference electrodes are shared for multiple working electrodes and sensing elements. In some implementations, external counter and reference electrodes are used. In other implementations, surface patterned on-chip counter and reference electrodes are used.

In some embodiments, the working electrode, the counter electrode, the reference electrode, and the sensing element are immersed in the buffered solution.

The working electrode and sensing element can have various shapes and sizes. In some implementations, the sensing element functions as working electrode. In some implementations, the sensing element and the working electrode are distinct electrodes. The sensing element may need physical separation from the working electrode to avoid a crosstalk or shorting. In some implementations, the sensing element is positioned in the same plane as the working electrode with a small gap therebetween to provide physical separation. The gap between the sensing element and the working electrode may range from, for example, 1 nanometer to 100 microns. In other implementations, the sensing element is placed on top of the working electrode with an insulation layer therebetween to provide physical separation.

In some implementations, the counter electrode is patterned around the working electrode, which minimizes the diffusion effect and helps controlling pH with a more definitive shape of the pH modulation zone.

The sensing element may comprise an ion-sensitive field-effect transistor (ISFET) or a metal oxide electrode such as thallium oxide electrode, aluminum oxide electrode, tin oxide electrode, zinc oxide electrode, ruthenium oxide electrode, titanium dioxide electrode, or iridium oxide electrode. An ISFET is a particular type of chemically-sensitive field-effect transistor (chemFET) that has sensitivity to the ion concentration in a solution. An ISFET is similar to a metal-oxide-semiconductor field-effect transistor (MOSFET) and has a source terminal (S), drain terminal (D), and a body (or bulk) connection. However, instead of a metal gate electrode, the ISFET has an ion-sensitive area immersed in a solution and a separate reference electrode. The ISFET may be configured to be sensitive to ions, for example hydrogen ions, and thus the pH of a solution.

Suitable sensing elements also include electrodes coated with a pH sensitive coating. Such coating may include, for example, an organic or an inorganic material. In some embodiments, the pH sensitive coating comprises a material selected from the group consisting of polyaniline, polypyrrole, polyaminoanthracene, polycarbazole, polybisphenol A, polyethyleneimine, poly(p-phenylenediamine), poly-1,5-diaminonaphthalene, titanium nitride, thallium oxide, aluminum oxide, tin oxide, zinc oxide, ruthenium oxide, and iridium oxide.

The closed-loop device may include, for example, multiple ISFETs that are used in a differential fashion in order to read and control the ion concentration and pH in a closed-loop system. The electrodes are composed of materials including, for example, metal oxide, glassy carbon, graphene, metal, gold, silver, platinum, conducting polymer, silver chloride, normal hydrogen, mercury drop, saturated calomel, or a combination thereof. In some implementations, the electrodes are patterned on a support including, for example, a glass slide, a plastic plate, a silicon wafer, a glass wafer, a quartz wafer, a flexible plastic sheet, a polymer layer, a paper, or a combination thereof.

The closed-loop device may use an open circuit potential (OCP) as a feedback measurement to control the current or potential. Suitable electrical control units include, but are not limited to, electronics that have current/voltage source output and sense input, and software that controls electrical parameters. Suitable materials, device design, configurations of electrical components, and controlling methods for the closed-loop device include those described in U.S. Pat. No. 10,379,080 and U.S. application Ser. No. 16/931,727 ("Closed-loop pH control with differential sensor," filed on Jul. 17, 2020), the entire contents of which are incorporated herein by reference.

The pH modulation of the present method may be carried out by applying current or voltage to the electrode. The electric potential or current used herein for pH modulation may be defined by a waveform capable of being modulated based on closed-loop control scheme to change the size of the pH modulated zone. For example, the size of the pH modulated zone adjacent to the surface of the electrode may be controlled by adjusting the parameters of the waveform.

The present method may include the following steps for detecting the change of ionic strength of the buffered solution with the closed-loop device:

(c1) controlling the current or voltage applied to the working electrode, thereby modulating the pH value in the zone between a first target pH value and a second target pH value.

(c2) measuring one or more parameters of the closed-loop device; and (c3) quantitating the change of ionic strength of the buffered solution from the one or more parameters.

The first and second target pH values may be selected based on the pH modulating agent, the types of the chemical reaction being studied, the buffering agent, and the ion strength of the buffered solution. The difference between the first and second target pH values may range from about 0.5 pH units to about 3.0 pH units, such as a difference of about 1.0 pH unit, about 1.5 pH units, about 2.0 pH units, or about 2.5 pH units. For example, the first and second target pH values may be about 6.0 and about 8.5, about 6.0 and about 8.0, about 6.0 and about 7.5, about 6.0 and about 7.0, about 6.5 and about 8.5, about 6.5 and about 8.0, about 6.5 and about 7.5, about 7.0 and about 8.5, or about 7.0 and about 8.0. In some embodiment, the first and second target pH values are 1.5 pH units or 2.0 pH units apart. In some embodiment, the first and second target pH values are about 6.0 and about 8.0, or about 6.0 and about 7.5.

The biological/chemical reaction may cause a change in the ion concentration and ion strength in the solution, while the pH of the solution is virtually constant pH due to the strong buffering capacity of the bulk solution. The localized pH modulation provided by the closed-loop device may serve as an additional perturbation to the buffered solution. At the same time, the ion strength of the solution may affect the ability of the closed-loop device to cycle between the target pH values. As the ion strength of the buffered solution changes, the electrical parameters of the closed-loop device need to be adjusted accordingly in order to maintain the pH modulation between two pre-determined pH values. The rates for the pH modulation reactions (e.g., oxidation/reduction of quinone derivatives) may also change in response to the change of ion strength in the bulk solution, which may be detected by the closed-loop device as alterations in parameters such as rise time, decay time, or slope.

Thus, the changes in the closed-loop device parameters in response to the change of ion strength in the solution may be monitored to detect the degree and progress of biological/chemical reactions and/or to evaluate the experimental condition, even before the pH change of the solution may be detected with a conventional method.

Suitable parameters of the closed-loop device may include: the current or voltage applied to the working electrode, the first target pH value, the second target pH value, pulse duration at the first target pH value (ts1), pause duration at the second target pH value (ts2), pH rise time (t1), pH decay time (t2); rise peak current (c1), stable current (c2), decay peak current (c3), current rise time (t3), and current decay time (t4).

In some embodiments, the first target pH value, the second target pH value, pulse duration at the first target pH value (ts1) and pause duration at the second target pH value (ts2) may be set at a pre-determined value. The closed-loop algorithm continuously controls the current or voltage needed to be applied to the working electrode based on the difference between the current pH value and the target pH value. pH modulation is performed by repeating the cycle composed of the pulse duration at the first target pH value (ts1) and pause duration at the second target pH value (ts2). In some embodiments, one or more parameters selected from pH rise time (t1), pH decay time (t2), rise peak current (c1), stable current (c2), decay peak current (c3), current rise time (t3), and current decay time (t4) are measured by the closed-loop device during each cycle of pH modulation.

In some embodiments, the present method includes the steps of:
(A) iteratively performing the following for the first target pH:
  measuring the signal output of the sensing element;
  selecting an amount of current to be applied to the working electrode in order to minimize the difference between the signal output of the sensing element and the first target sensing value;
  applying the specifically selected amount of current to the working electrode to change the pH of the local solution close to the working electrode;
  determining, with the electronic controller, a voltage required for the amount of current, time for the current to reach a stable value;
  determining, with the electronic controller, a time for the pH to reach the first target pH; and
(B) iteratively performing the following for the second target pH:
  measuring the signal output of the sensing element;
  selecting an amount of current to be applied to the working electrode in order to minimize the difference between the signal output of the sensing element and the second target sensing value;
  applying the specifically selected amount of current to the working electrode to change the pH of the local solution close to the working electrode;
  determining, with the electronic controller, a voltage required for the amount of current, time for the current to reach a stable value;
  determining, with the electronic controller, a time for the pH to reach the second target pH.

Representative Process of Monitoring a Chemical Reaction

Figure 1:
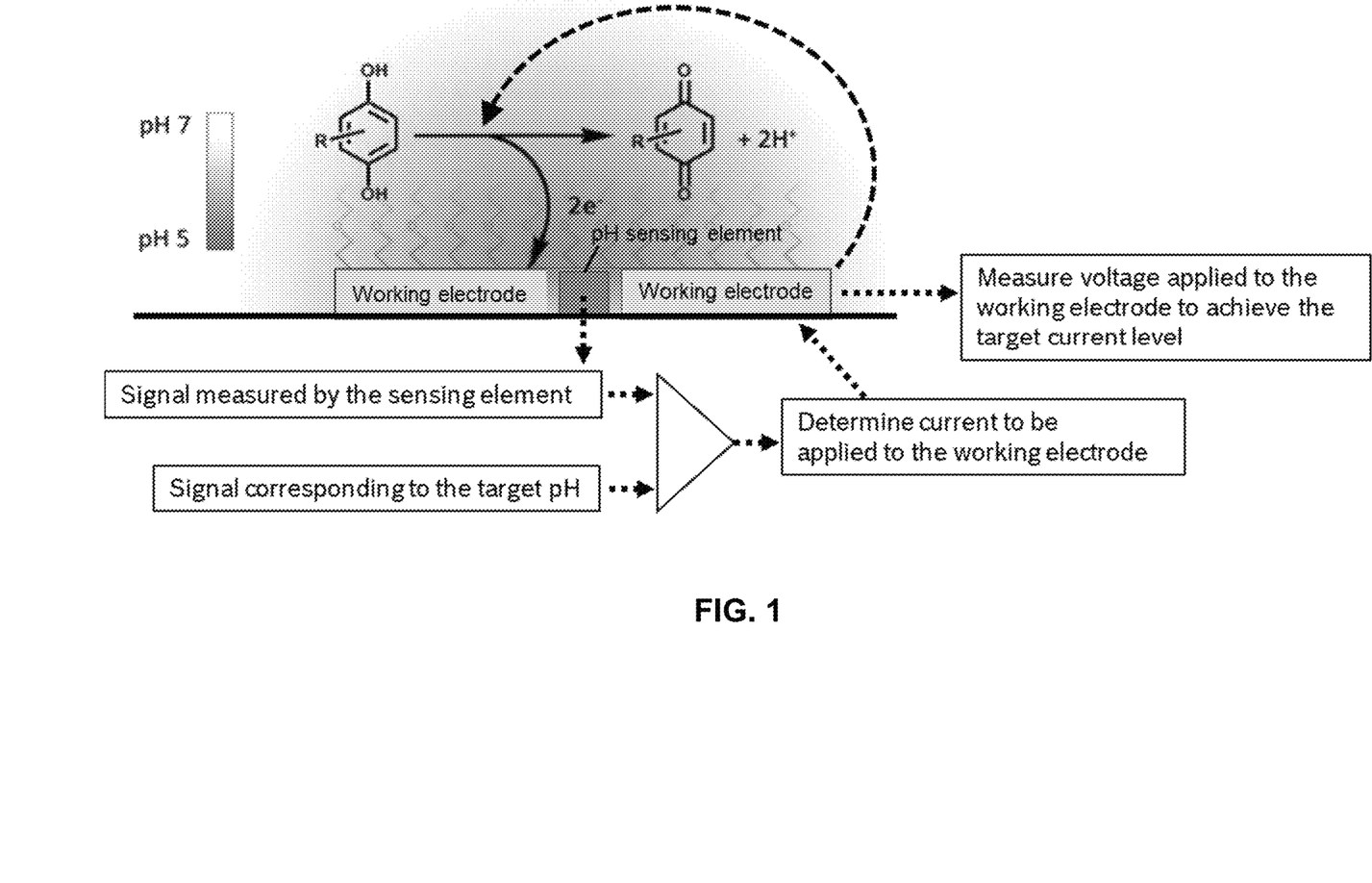
FIG. 1 shows a schematic for modulating pH of a solution via oxidation/reduction of redox active species (in this example, quinones) with a closed-loop control.

A process is developed for monitoring ion concentration change of a buffered solution by measuring the electrical parameters of closed-loop device during a localized, electrochemical pH modulation. FIG. 1 shows a schematic for the electrochemical pH modulation with surface patterned electrodes. The electrical configuration is composed of a working electrode, a pH sensing element, a counter electrode, and a reference electrode. pH modulating agents that either generate or consume protons during reaction are added to the sample solution. The pH sensing element measures the initial pH values from which the amount of current or voltage that needs to be applied to the working electrode is calculated. When the current or voltage is applied to the working electrode, electrochemical oxidation and/or reduction of pH modulating agents introduces a local pH change through the equilibration between generation or consumption of protons and buffering capacity of the buffer solution. This local pH change generates a pH modulation zone with a very short vertical distance—several nm to several mm—from the surface of the electrode. Since the size of the pH modulation zone is dependent on the equilibration between altered proton amount and the buffering capacity, the buffer strength of the solution is an important controlling factor. Monitoring the actual pH during the modulation with the pH sensing element allows to change the electrical output continuously through a closed-loop control, which enables a faster and more precise pH control. In the closed-loop control, the amount of current/voltage that needs to be applied to the working electrode to create a target change in pH depends on the ionic strength and buffering capacity of the solution. Advantageously, the change in ionic strength of a solution may be measured by the present method while the pH of solution is still constant.

Figure 2:
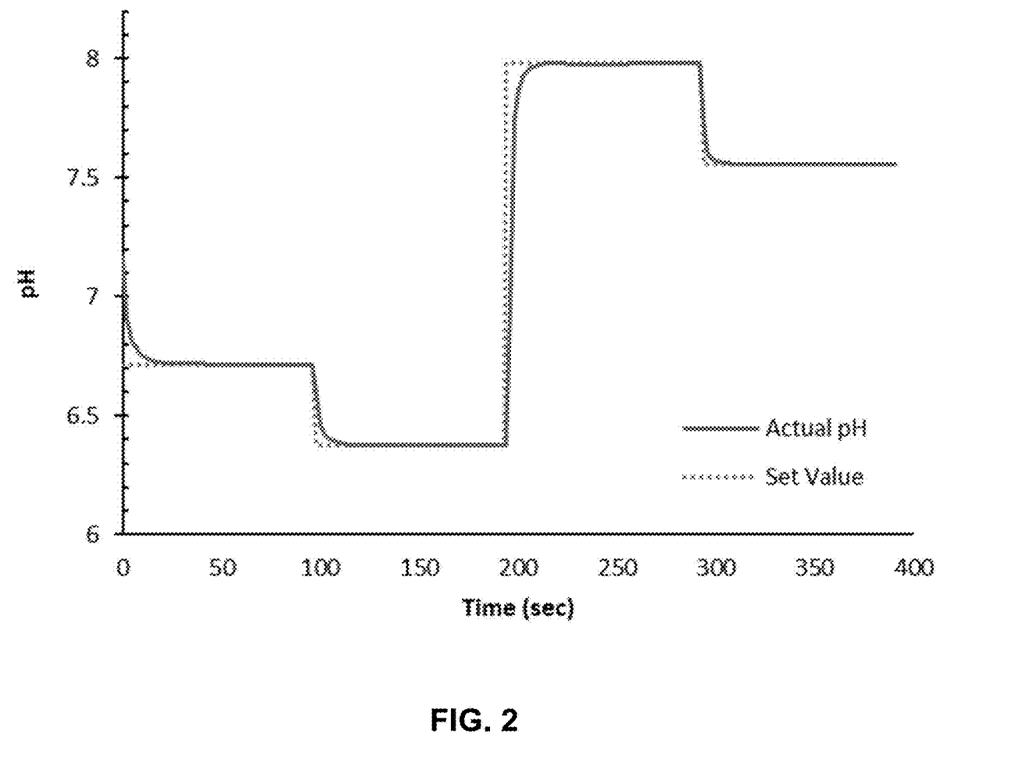
FIG. 2 shows an example of changing pH of a solution via oxidation/reduction of quinones in 1 mM phosphate buffer on indium tin oxide electrode. The pH values were determined by a pre-calibrated iridium oxide sensing electrode patterned on the surface and the closed-loop control achieved the target pH values in an accurate and rapid manner. In representative processes, modulation of pH near the surface of the working electrode is achieved while the pH of the bulk solution is kept constant by a strong buffer.

Reversible electrochemical oxidation/reduction of pH modulating agents such as quinone derivatives, hydrazine derivatives, or water have been demonstrated for a rapid pH change in a local region. The pH modulation limit depends on the pKa and oxidation/reduction potential of the specific pH modulation reagents, and their concentration. FIG. 2 demonstrates the multi-step pH modulation by the oxidation of 2,5-dimethyl-1,4-hydroquinone and the reduction of the 2,5-dimethyl-1,4-benzoquinone on an indium-tin oxide electrode in 1 mM phosphate buffer. When anodic current is applied to the electrode, the proton production overcomes the buffer capacity and pH of the solution becomes more acidic and vice versa.

Electrochemical pH modulation with a closed-loop control involves a set of electrodes: a working electrode, a sensing element, a counter electrode, and a reference electrode. Those electrodes may be any form including external electrodes, device-integrated/surface patterned electrodes, etc. Multiple electrode sets can be used to improve reliability, uniformity, and speed. For the sensing element, an electrode coated with a pH sensitive material may be a common configuration. However, a semiconductor-based electrical component such as field-effect transistors or polymer semiconductor can also be used. Especially, an ion-sensitive field-effect transistor (ISFET) is a particular type of chemically-sensitive field-effect transistor (chemFET) that has sensitivity to the ion concentration in a solution. The counter electrode and the reference electrode may be shared for multiple working electrodes and sensing elements. Since the role of the reference electrode is providing a stable potential reference for the measurement, it may be an option that a sensing electrode is used as a reference electrode, if it has a good stability and is placed in a stable pH solution.

Figure 3:
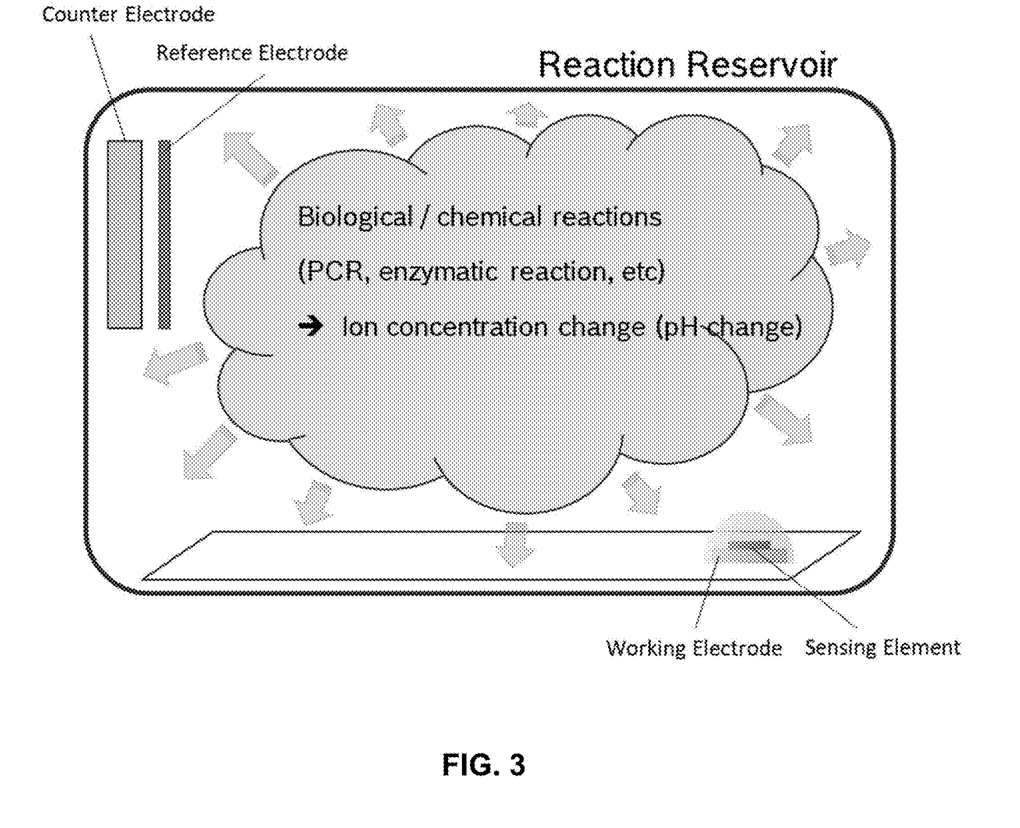
FIG. 3 shows the ion concentration change induced by biological or chemical reactions and sensing components.
Figure 4:
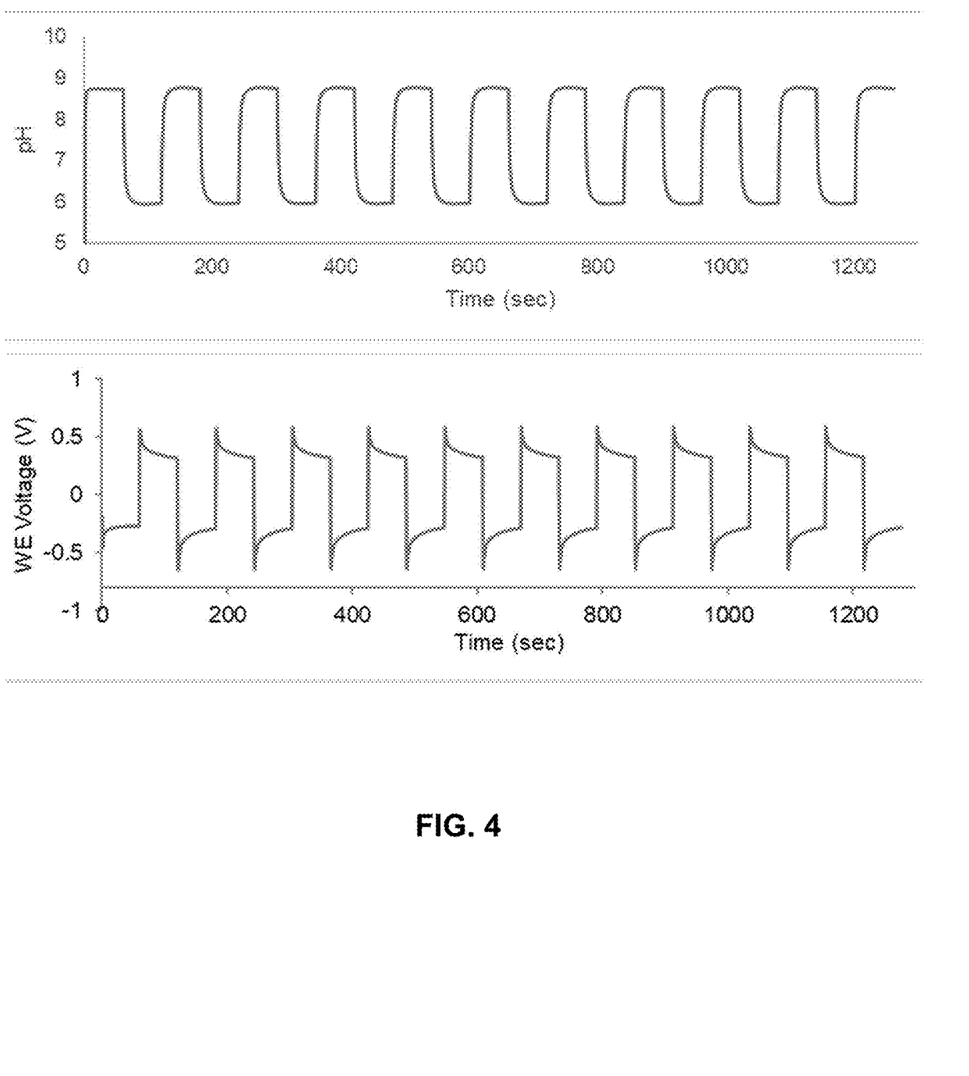
FIG. 4 shows an example of the pH modulation cycles between two pH values (top) and the corresponding required voltage to the working electrode (bottom).

FIG. 3 illustrates that a biological/chemical reaction may introduce ion concentration change as reaction progresses. At least one set of the working electrode and the sensing element is located in the same sample solution. Electrochemical pH modulation with closed-loop control can continuously perform pH modulation between at least two pre-determined pH values with a high accuracy and a high speed. FIG. 4 shows an example of pH modulation cycles between two pH values. Typically, pH changes only within the small pH modulation zone without affecting the bulk pH value (FIG. 4, top panel). A trace of the voltage is applied to the working electrode to achieve assigned pH change (FIG. 4, bottom panel). Depending on the difference between the actual pH of the pH modulation zone and the set pH value, the current level determined by the closed-loop algorithm changes. The current is applied to the working electrode and the resulting voltage on the working electrode is monitored (FIG. 4, bottom panel).

Figure 5:
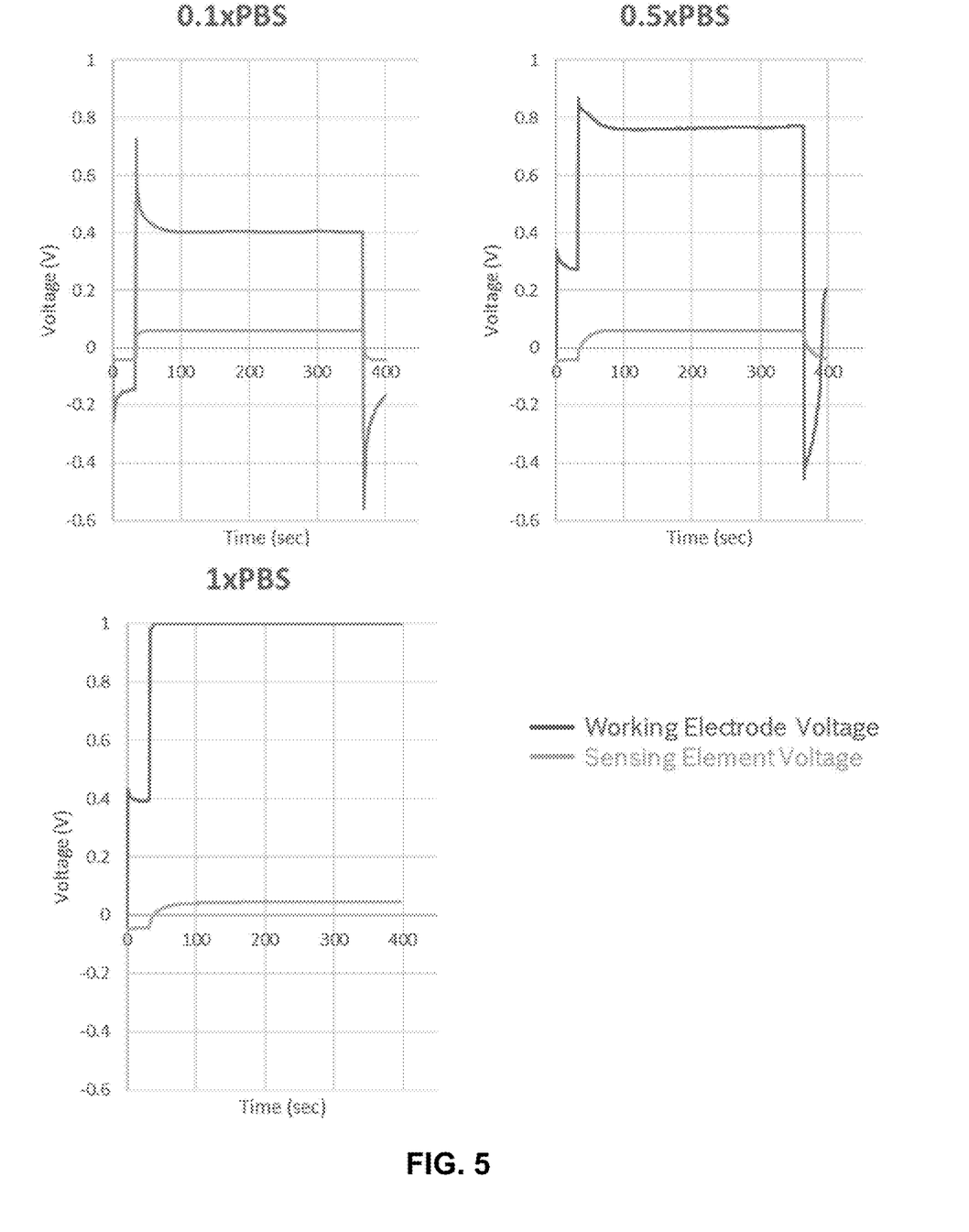
FIG. 5 shows an example of the electrical parameter changes for the pH modulation under different buffer capacity. To achieve the pH change of 2 pH units (shown as the voltage output of the sensing element depicted in orange line), higher working electrode voltage is needed as buffer strength of the solution increases. At high buffer capacity (1xPBS) in this example, the target pH change was not fully achieved even when the working electrode voltage reached the limit (1V) of the hardware. Target pH change may be selected depending on the buffering agent, the pH modulating agent, and the chemical reaction being studied.
Figure 6:
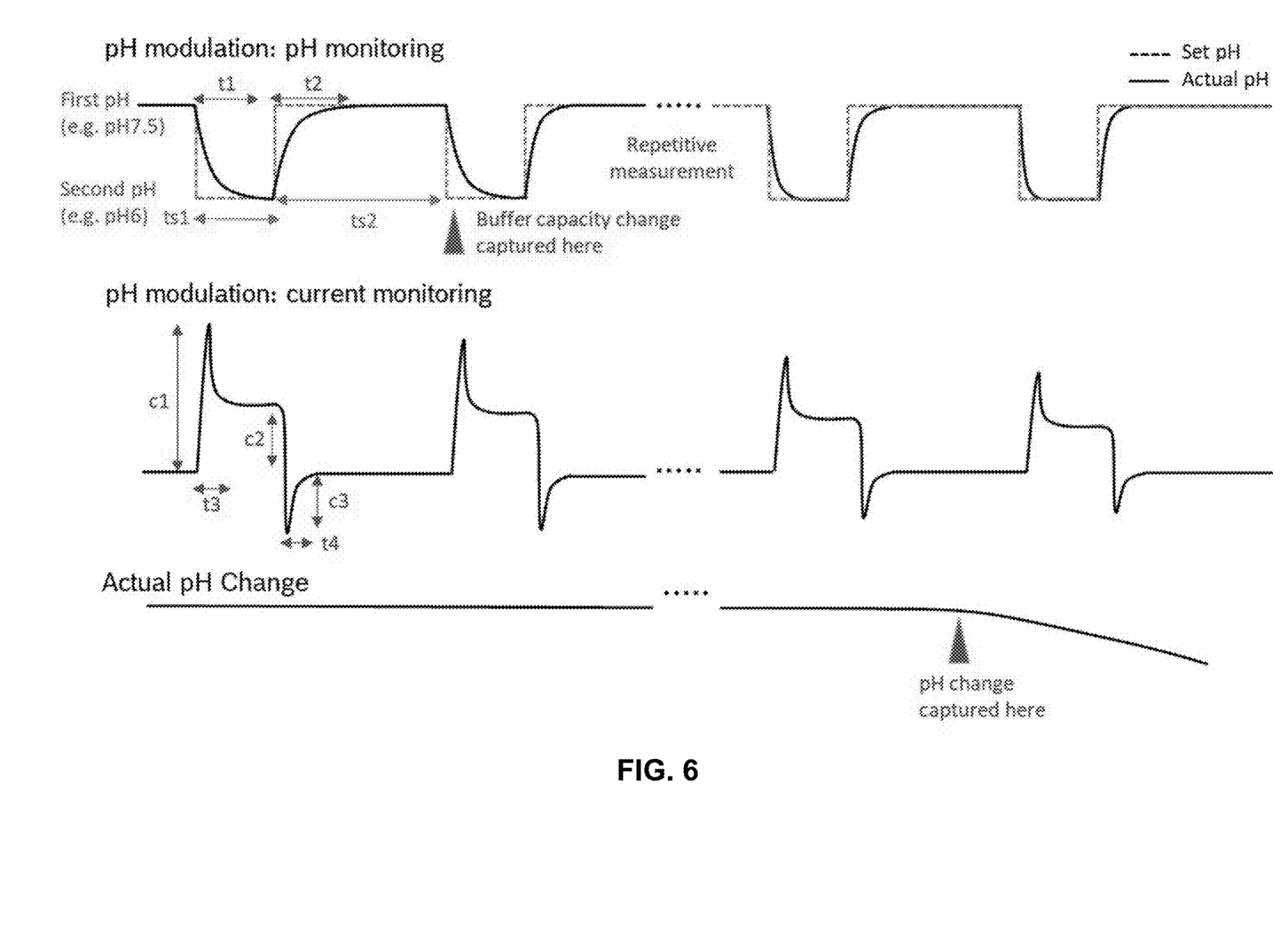
FIG. 6 shows a representative pH-modulation-based ion strength monitoring using a closed-loop device. Actual pH modulation trajectory is monitored over time, as pH modulation between two values are performed (top). Required current values to achieve the target pH values are monitored continuously (middle). Actual pH change may be captured at later time point than the present method (bottom). In representative processes, the required parameters of the closed-loop device (such as the time and current/voltage) to achieve the target pH values change over time, in response to the change of ionic strength of the solution as the reaction proceeds.

FIG. 5 shows an example of the electrical parameters change as the buffer capacity and ion strength of the solution increases from 0.1×PBS (10-fold diluted buffer) to 1×PBS (no dilution). A higher voltage is needed to achieve the same level of pH change in a solution with higher buffer capacity and ion strength. FIG. 6 illustrates a more detailed example of the parameters of the closed-loop device that may be measured to monitor the change of ion strength in the present method. For pH modulation, there are at least 4 input parameters that may be monitored: first pH set-value, second pH set-value, pH modulation pulse duration (ts1), and pause duration (ts2). From pH monitoring, pH rise time (t1) and pH decay time (t2) may be monitored. From electrical monitoring, rise peak current (c1), stable current (c2), decay peak current (c3), current rise time (t3), and current decay time (t4) may be monitored. These parameters are non-limiting examples for the present method and may be changed for specific experimental designs. The changes of the values of these parameters may be used to quantify the degree and progress of reactions of interest.

In an example implementation, the present method is used to monitor DNA replication by qPCR. As shown in FIG. 6, the pH modulation is controlled by the closed-loop device with repeated cycles between pH 6 and pH 7.5 targets (top panel). The DNA amplification reaction occurring in the sample solution causes a change in the ion strength in the bulk solution, while the pH is kept at a constant level by a strong buffer. However, as the ion concentration of the buffered solution changes, the required electrical parameters of the closed-loop device change accordingly in order to maintain the pH modulation between the two target pH values (e.g., decrease of the magnitude of c1 and c3, middle panel), which are detected by the closed-loop device. As the reaction progresses further, the actual pH of solution changes due to the release of $H^+$ may be recorded (bottom panel). Remarkably, the present method may detect the change of ion strength resulting from the reaction at an earlier time point than that of direct measurement of pH change in the solution (top and bottom panels). Thus, the present method has the advantage of maintaining a stable pH environment in a buffered solution for an enzyme (e.g., DNA polymerase) to function consistently, while being able to probe the change in solution buffering capacity to quantify the change in proton concentration during the PCR reaction, preventing the need for deconvolution.

Various features, advantages, and embodiments are set forth in the following claims.

What is claimed is:

1. A method for monitoring a chemical reaction, comprising
   (a) starting the chemical reaction in a buffered solution equipped with a closed-loop device, wherein
      the buffered solution comprises a pH modulating agent;
      the closed-loop device comprises an electronic controller, a working electrode, a counter electrode, a reference electrode, and a sensing element, wherein the working electrode, the counter electrode, the reference electrode, and the sensing element are immersed in the buffered solution, and wherein the sensing element is positioned on top of the working electrode with an insulation layer therebetween to provide physical separation; and
      the chemical reaction causes a change of ionic strength of the buffered solution;
   (b) applying a current or voltage to the working electrode, whereupon the pH modulating agent causes a continuous cycling of pH modulation between at least two target pH values in a zone adjacent to a surface of the working electrode and the sensing element;
   (c) detecting the change of ionic strength of the buffered solution with the closed-loop device, wherein the detecting comprises:
      (c1) controlling the current or voltage applied to the working electrode, thereby modulating the pH value in the zone between the at least two target pH values;
      (c2) analyzing the current or voltage applied to the working electrode and a signal output from the sensing element; and
      (c3) quantitating the change of ionic strength of the buffered solution from the current or voltage applied to the working electrode and the signal output from the sensing element; and
   (d) repeating steps (b) and (c) at least one time.

2. The method of claim 1, wherein detecting further comprises analyzing one or more additional parameters of the closed-loop device selected from the group consisting of: a first target pH value, a second target pH value, pulse duration at the first target pH value (ts1), pause duration at the second target pH value (ts2), pH rise time (t1), pH decay time (t2); rise peak current (c1), stable current (c2), decay peak current (c3), current rise time (t3), and current decay time (t4).

3. The method of claim 1, further comprising
   (e) determining the progress of the chemical reaction.

4. The method of claim 1, wherein the sensing element comprises
   an ion-sensitive field-effect transistor (ISFET);
   a metal oxide electrode selected from the group consisting of thallium oxide electrode, aluminum oxide electrode, tin oxide electrode, zinc oxide electrode, ruthenium oxide electrode, titanium dioxide electrode, and iridium oxide electrode; or
   an electrode coated with a pH sensitive coating, the pH sensitive coating comprising a material selected from the group consisting of polyaniline, polypyrrole, polyaminoanthracene, polycarbazole, polybisphenol A, polyethyleneimine, poly (p-phenylenediamine), poly-1,5- diaminonaphthalene, titanium nitride, thallium oxide, aluminum oxide, tin oxide, zinc oxide, ruthenium oxide, and iridium oxide.

5. The method of claim 1, wherein a bulk of the buffered solution apart from the zone adjacent to the surface of the working electrode maintains a constant pH value.

6. The method of claim 1, wherein the buffered solution comprises a buffering agent selected from the group consisting of phosphate, TAPS, Bicine, Tris, Tricine, TAPSO, HEPES, TES, MOPS, PIPES, cacodylate, SSC, and MES.

7. The method of claim 6, wherein a concentration of the buffering agent in the buffered solution is at least 1 mM.

8. The method of claim 1, wherein the chemical reaction produces $H^+$ or $OH^{31}$.

9. The method of claim 1, wherein the chemical reaction is a DNA amplification reaction.

10. The method of claim 1, wherein the chemical reaction is a quantitative Polymerase Chain Reaction (qPCR).

11. The method of claim 1, wherein the pH modulating agent is a quinone derivative, an aminophenol derivative, an aniline derivative, a benzidine derivative, a hydrazine derivative, or a combination thereof.

12. The method of claim 1, wherein the pH modulating agent is a quinone derivative of any of formula (I)-(XII)

(II)

(III)

(IV)

(V)

(VI)

(VII)

(VIII)

(IX)

(X)

(XI)

X = C or N (XII)

X = C or N wherein $R_1$, $R_2$, $R_3$, $R_4$, $R_5$, $R_6$, $R_7$, and $R_8$ are each independently selected from the group consisting of: H; $C_nH_{2n+1}$; Cl; F; I, Br, OM, $NO_2$, OH, $OC_nH_{2n+1}$, $OC_nH_{2n}OH$, $O(C_nH_{2n}O)_yH$, $O(C_nH_{2n}O)_yC_nH_{2n+1}$, $O(C_nH_{2n}O)_yCOOH$; $O(C_nH_{2n}O)_yCOOM$; COOH; COOM; $COOC_nH_{2n+1}$; $CONHC_nH_{2n+1}$; $CON(C_nH_{2n+1})_2$; $SO_3H$; $SO_3M$; $NH_2$; $NHC_nH_{2n+1}$; $N(C_nH_{2n+1})_2$; $NHC_nH_{2n}OH$; $NHC_nH_{2n}NH_2$; $N(C_nH_{2n}OH)_2$; $N(C_nH_{2n}NH_2)_2$; $NHCOC_nH_{2n+1}$; $NC_nH_{2n}COC_nH_{2n+1}$; $NC_nH_{2n}COC_nH_{2n}OH$; $NC_nH_{2n}COC_nH_{2n}NH_2$; $NHC_nH_{2n}COC_nH_{2n}SH$; SH; $SC_nH_{2n+1}$; $SC_nH_{2n}OH$; $S(C_nH_{2n}O)_yH$; $S(C_nH_{2n}O)_yC_nH_{2n+1}$; $S(C_nH_{2n}O)_yCOOH$; $S(C_nH_{2n}O)_yCOOM$; $OC_nH_{2n}SH$; $O(C_nH_{2n}O)_yC_nH_{2n}SH$; $O(C_nH_{2n}O)_yC_nH_{2n}SC_nH_{2n+1}$; $C_nH_{2n}OC_nH_{2n+1}$; $C_nH_{2n}SC_nH_{2n+1}$; $C_nH_{2n}NHC_nH_{2n+1}$; $C_nH_{2n}OH$; $C_nH_{2n}OC_nH_{2n+1}$; $C_nH_{2n}OC_nH_{2n}OH$; $C_nH_{2n}O(C_nH_{2n}O)_yCOOH$; $C_nH_{2n}O(C_nH_{2n}O)_yCOOM$; $C_nH_{2n}COOH$; $C_nH_{2n}COOM$; $C_nH_{2n}COOC_nH_{2n+1}$; $C_nH_{2n}CONHC_nH_{2n+1}$; $C_nH_{2n}CONH(C_nH_{2n+1})_2$; $C_nH_{2n}SO_3H$; $C_nH_{2n}SO_3M$; $C_nH_{2n}NH_2$; $C_nH_{2n}N(C_nH_{2n+1})_2$; $C_nH_{2n}NHC_nH_{2n}OH$; $C_nH_{2n}NHC_nH_{2n}NH_2$; $C_nH_{2n}N(C_nH_{2n}OH)_2$; $C_nH_{2n}N(C_nH_{2n}NH_2)_2$; $C_nH_{2n}NHCOC_nH_{2n+1}$; $C_nH_{2n}NHC_nH_{2n}COC_nH_{2n}OH$; $C_nH_{2n}NHC_nH_{2n}COC_nH_{2n}NH_2$; $C_nH_{2n}NHC_nH_{2n}COC_nH_2SH$; $C_nH_{2n}SH$; $C_nH_{2n}SC_nH_{2n+1}$; $C_nH_{2n}SC_nH_{2n}OH$; $C_nH_{2n}S(C_nH_{2n}O)_yH$; $C_nH_{2n}S(C_nH_{2n}O)_y C_nH_{2n+1}$; $C_nH_{2n}S(C_nH_{2n}O)_yC_nH_{2n}COOH$;

$C_nH_{2n}S(C_nH_{2n}O)_yC_nH_{2n}COOM$; sugars; peptides; and amino acids,
wherein
M is any metal cation or $NH_4^+$,
n is an integer from 1 to $10^9$, and
y is an integer from 1 to $10^9$.

* * * * *